(12) United States Patent
Gillece et al.

(10) Patent No.: US 9,327,143 B2
(45) Date of Patent: May 3, 2016

(54) USE OF POLYELECTROLYTE COMPLEXES IN ANTIPERSPIRANT TECHNOLOGY

(75) Inventors: Timothy W. Gillece, Hackettstown, NJ (US); Linda C. Foltis, Nutley, NJ (US); Donald F. Koelmel, Asbury, NJ (US); Anthony Neil Luschen, Wayne, NJ (US); Christine Marie Barrett, Oakland, NJ (US)

(73) Assignee: ISP INVESTMENTS INC., Wilmington, DE (US)

( * ) Notice: Subject to any disclaimer, the term of this patent is extended or adjusted under 35 U.S.C. 154(b) by 374 days.

(21) Appl. No.: 12/812,078

(22) PCT Filed: Jan. 14, 2009

(86) PCT No.: PCT/US2009/030947
§ 371 (c)(1),
(2), (4) Date: Aug. 13, 2010

(87) PCT Pub. No.: WO2009/091794
PCT Pub. Date: Jul. 23, 2009

(65) Prior Publication Data
US 2010/0297201 A1 Nov. 25, 2010

Related U.S. Application Data

(60) Provisional application No. 61/020,873, filed on Jan. 14, 2008.

(51) Int. Cl.
*A61K 8/02* (2006.01)
*A61Q 15/00* (2006.01)
*A61K 8/81* (2006.01)
*A61K 8/27* (2006.01)
*A61K 8/29* (2006.01)

(52) U.S. Cl.
CPC .............. *A61Q 15/00* (2013.01); *A61K 8/8164* (2013.01); *A61K 8/8182* (2013.01); *A61K 8/27* (2013.01); *A61K 8/29* (2013.01); *A61K 2800/5424* (2013.01); *A61K 2800/5426* (2013.01); *A61K 2800/594* (2013.01)

(58) Field of Classification Search
None
See application file for complete search history.

(56) References Cited

U.S. PATENT DOCUMENTS

| | | |
|---|---|---|
| 2004/0166081 A1 | 8/2004 | Ulmer et al. |
| 2005/0186163 A1 | 8/2005 | Li et al. |
| 2006/0067901 A1 | 3/2006 | Bertz et al. |
| 2006/0183822 A1* | 8/2006 | Nguyen-Kim et al. ......... 524/35 |
| 2006/0251603 A1 | 11/2006 | Rigoletto, Jr. et al. |
| 2007/0142255 A1* | 6/2007 | Qiu ............................... 510/130 |

OTHER PUBLICATIONS

Goddard and Gruber, *Principles of Polymer Science and Technology in Cosmetics and Personal Care*, Marcel Dekker, Inc. (1999), 3 pages.

* cited by examiner

*Primary Examiner* — James Rogers
(74) *Attorney, Agent, or Firm* — Thompson Hine LLP; William J. Davis

(57) ABSTRACT

Polyelectrolyte complexes between cationic polymers and anionic polymers are used in antiperspirant compositions containing an active antiperspirant ingredient.

22 Claims, 4 Drawing Sheets

Gantrez® S-97:Conditioneze® NT-20 PEC 2.2% Gantrez® S-97:Conditioneze® NT-20 PEC : 6.7% AACH 2.2% Gantrez® S-97:Conditioneze® NT-20 PEC : 2.2% AACH : 4.4% CaCl$_2$ Flow Curve for Gantrez® S-97:Conditioneze® NT-20 PEC + 5%CaCl$_2$ + 1% AACH

USE OF POLYELECTROLYTE COMPLEXES IN ANTIPERSPIRANT TECHNOLOGY

CROSS REFERENCE TO RELATED APPLICATION

This application claims the benefit of U.S. Provisional Application Ser. No. 61/020,873 filed Jan. 14, 2008, the contents of which are hereby incorporated by reference.

FIELD

The present application relates to antiperspirant compositions and, more particularly, to antiperspirant compositions containing a polyelectrolyte complex.

BACKGROUND

Antiperspirant compositions are well known in the art. See, e.g., U.S. Pat. Nos. 4,985,238; 5,302,381; 5,376,362; 5,417,963; 5,482,702; and 5,486,355, the disclosures of which are hereby incorporated by reference. The active antiperspirant ingredient in such compositions usually is an inorganic compound, e.g., an aluminum, zirconium, or zinc salt such as an aluminum zirconium tetrachlorohydrate complex with glycine.

Polyelectrolyte complexes (PEC) between anionic and cationic polymers form microgels. Examples of these polyelectrolyte complexes are described in U.S. Patent Application Publication Nos. 2006/0251603, filed Jul. 11, 2006 and 2005/0089494, filed Jul. 14, 2004, the contents of which are hereby incorporated by reference.

SUMMARY

The present application relates to an antiperspirant composition containing an active antiperspirant ingredient and a polyelectrolyte complex between a cationic polyquaternium polymer and an anionic polymer. In accordance with particular aspects of the present invention, the anionic polymers include those polyacids containing mono-, di- or tri-acid monomers or their neutralized salts. In accordance with another aspect of the present invention, the cationic polymer and anionic polymer are present at a charge ratio of about 0.70 to 1.80, more particularly from about 0.90 to about 1.50, respectively.

The antiperspirant composition of the present invention may take the form of an antiperspirant stick, lotion, cream, roll-on, solution or aerosol.

In accordance with particular aspects of the present invention, the active antiperspirant ingredient may be an activated aluminum chlorohydrate, degraded activated aluminum chlorohydrate or aluminum chlorohydrate.

DETAILED DESCRIPTION

Figure 1:
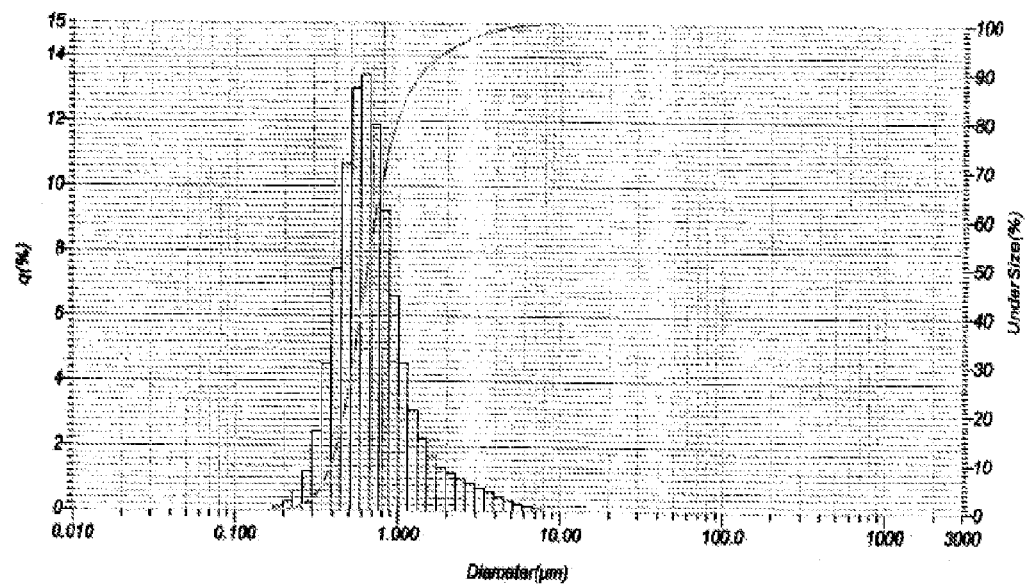
FIG. 1 is a graphical plot of particle size distribution of an aqueous Gantrez® S-97:Conditioneze® NT-20 PEC alone.

The present application relates to antiperspirant compositions containing a polyelectrolyte complex formed between cationic and anionic polymers.

A complex is formed herein between two polymers interacting through non-covalent bonding e.g. ionic, hydrogen, or an associative mechanism of hydrophobic groups on the molecule. In accordance with certain aspects, two oppositely charged polymers interact through their cationic and anionic charges to form a polyelectrolyte complex in the form of a microgel.

In an antiperspirant composition of certain embodiments, the polyelectrolyte complex is in the form of microgels having an average particle size in the range of 0.5 µm to 100 microns which are small enough to enter the pores of the sweat gland, thereby forming polymeric plugs to impact sweat reduction.

The particle size distribution of microgels of the complex in water was measured using a Malvern Mastersizer S. This instrument determines the particle size distribution of liquid dispersions using Mie laser light scattering theory. In accordance with a particular embodiment, the microgel particles without an active ingredient have a mean diameter of 6.70 µm and the size ranges from 0.53 µm at 10% distribution to 31.68 µm at 90% distribution.

One example of a cationic/anionic polymer polyelectrolyte complex used herein is a complex of Gantrez® S-97 and Conditioneze® NT-20. At a defined cationic/anionic ratio the polyelectrolyte complex is present as microgels as illustrated in the example below. In this system, the cationic nature of Conditioneze® NT-20 contributes to the residual cationic charges on the microgels. Then the PEC microgels' adhesive crosslinking structure can seal the pores on drying through the dry film formed.

Examples of such cationic polyquaternium polymers are polyquaternium compounds including, but not limited to, Polyquaternium 6, 10, 11, 7, and 28 which have trade names as Merquat®, Polyquta®, Gafquat®, Conditioneze® 7 and Conditioneze® 28, respectively. Quaternized polysaccharides are other examples of suitable cationic polymers, e.g. Guar Hydroxypropyltrimonium chloride having the trade name Jaguar® (Rhodia).

Examples of anionic polymers include those polyacids containing mono-, di- or tri-acid monomers or their neutralized salts. The polyacids containing di-acid units include, but are not limited to, polyvinylmethyl/maleic acid (PVM/MA) copolymer which has a trade name Gantrez® S-97 (ISP). Examples of polyacid or salt with a mono-acid unit include, but not limited to, the acrylic acid copolymers, or their salts, such as vinylpyrrolidone/acrylates/lauryl methacrylate copolymer which has a trade name of Styleze® 2000 (ISP).

Additional examples of cationic and anionic polymers of synthetic or natural origin can be found in the following treatises which disclose ingredients used in the personal care industry, and are included herein for reference: *Encyclopedia of Polymers and Thickeners, Cosmetic and Toiletries*, Vol. 117, No. 12. December 2002; *Cosmetic Raw Material Analysis and Quality*, Chapter 3, IFSCC, Monograph, 2004; *Principles of Polymer Science and Technology in Cosmetics and Personal Care,* 1999, Appendix.

A typical cationic polymer for forming the PEC has the chemical structure set forth below.

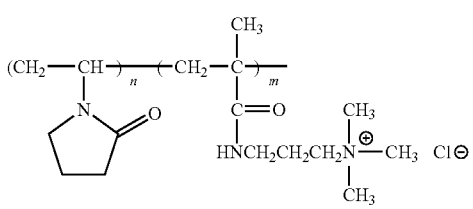

Conditioneze® NT-20 (Polyquaternium-28)
(wt. Molecular wt. of about 1 Million, and a Weight Ratio of n and m of 85:15)

The chemical structure of a typical anionic polymer which can form the polyelectrolyte complex in this invention is:

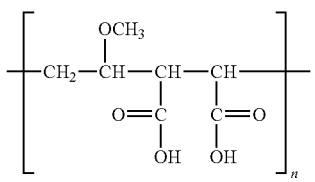

Gantrez® S-97 (PVM/MA Copolymer) (Specific Viscosity of Gantrez AN 169 is 2.5 to 3.5) (1% in MEK 25° C.)

By controlling the charge ratios of the two oppositely charged polymers, the complexation of the polymers can lead to the formation of a microgel structure.

In accordance with certain aspects, the PEC microgels have an average particle size ranging from about 0.5 μm to about 31 μm, from about 3 to about 15 microns. PEC microgels containing an active antiperspirant ingredient typically have an average particle size of from about 2 μm to about 100 μm, more particularly from about 5 μm to about 60 μm.

In certain cases, the charge ratio of the cationic to anionic polymers ranges from about 0.70-1.80, more particularly from about 0.90 to 1.5.

The mole ratio of the quaternium unit of the cationic polymer to the anionic polymer is the charge ratio times $n_a/n_c$, where $n_a$ is the total number of anionic groups in one monomer unit of the anionic polymer and $n_c$ is the total number of quaternary groups in one monomer unit of the cationic polymer.

For example, the $n_a$ of the anionic polymer polyvinylmethyl/maleic acid (PVM/MA), is 1.7 at pH 7, considering that one acid group having a low pKa is fully ionized and the other acid group having a higher pKa is 70% ionized, giving the total anionic number of 1.7 in its one monomer unit. Therefore, the mole ratio of the quaternium unit of the mono cationic polymer polyquaternium-28 to the anionic polymer containing a di-acid unit such as polyvinylmethyl/maleic acid (PVM/MA) may be about 1.39 to 3.06, more particularly 1.50 to 2.55.

Accordingly, the mole ratio of the quaternium unit of the cationic polymer to anionic polymer wherein the anionic polymer contains a mono-acid unit such as vinylpyrrolidone/acrylates/lauryl methacrylate may be about 0.82 to 1.80, more particularly is 0.90 to 1.50.

The weight ratio of the cationic polymer to the anionic polymer is the mole ratio times MWc times the wt. % of quaternary unit in the cationic polymer divided by MWa times the wt. % of the acid unit in the anionic polymer. MWc is the molecular weight of the monomer unit in the cationic polymer and MWa is the molecular weight of the monomer unit in the anionic polymer. For example, the weight ratio of a mono cationic polymer, e.g. polyquaternium-28, to the anionic polymer containing a di-acid unit such as polyvinylmethyl/maleic acid (PVM/MA) may be about 6 to 15, more particularly from 7.0 to 11.91.

Accordingly, the weight ratio of the cationic polymer e.g. polyquaternium-28, to the anionic polymer wherein the cationic polymer contains a mono-acid group, e.g. vinylpyrrolidone/acrylates/lauryl methacrylate, may be about 2.44 to 5.37, more particularly from 2.68 to 4.47.

Various active antiperspirant ingredients that can be utilized according to the present invention include conventional antiperspirant metal salts and complexes of metal salts. In one aspect of the invention the metal salts and metal salt complexes utilized as the active antiperspirant ingredients are acidic and are based on aluminum and zirconium and combinations thereof. These salts include but are not limited to aluminum halides, aluminum hydroxyhalides, aluminum sulfate, zirconium (zirconyl) oxyhalides, zirconium (zirconyl) hydroxyhalides, and mixtures or complexes thereof. Complexes of aluminum and zirconium salts include aluminum and zirconium salt complexes with amino acids, such as, for example, glycine or complexes with a glycol, such as, for example, propylene glycol (PG) or polyethylene glycol (PEG). Exemplary active antiperspirant ingredients include, but are not limited to, aluminum chloride, aluminum chlorohydrate, activated aluminum chlorohydrate, degraded activated aluminum chlorohydrate, aluminum dichlorohydrate, aluminum sesquichlorohydrate, zirconyl hydroxychloride, aluminum chlorohydrex PEG (aluminum chlorohydrex polyethylene glycol), aluminum chlorohydrex PG (aluminum chlorohydrex propylene glycol), aluminum dichlorohydrex PEG (aluminum dichlorohydrex polyethylene glycol), aluminum dichlorohydrex PG (aluminum dichlorohydrex propylene glycol), aluminum sesquichlorohydrex PEG (aluminum sesquichlorohydrex polyethylene glycol), aluminum sesquichlorohydrex PG (aluminum sesquichlorohydrex propylene glycol), aluminum zirconium trichlorohyrate, aluminum zirconium tetrachlorohyrate, aluminum zirconium pentachlorohyrate, aluminum zirconium octachlorohyrate, aluminum zirconium chlorohydrex GLY (aluminum zirconium chlorohydrex glycine), aluminum zirconium trichlorohydrex GLY (aluminum zirconium trichlorohydrex glycine), aluminum zirconium tetrachlorohyrex GLY (aluminum zirconium tetrachlorohyrex glycine), aluminum zirconium pentachlorohyrex GLY (aluminum zirconium pentachlorohyrex glycine), and aluminum zirconium octachlorohyrex GLY (aluminum zirconium octachlorohyrex glycine). Other active antiperspirant ingredients include ferric chloride and zirconium powder. Mixtures of any of the foregoing active antiperspirant ingredients are also suitable for use in the present invention.

The amount of the active antiperspirant ingredients incorporated into the compositions of the present invention is an amount that is sufficient to reduce the flow of perspiration from the location to which the antiperspirant product is applied, for example to the axillary area of the human body.

Generally, the level of active antiperspirant ingredients utilized in the compositions of the present invention ranges from about 0.5 wt. % to about 35 wt. % based on the total weight of the composition. In another aspect of the invention, the amount of active antiperspirant ingredient in the composition can range from about 5 wt. % to about 25 wt. %, in a further aspect from about 5 wt. % to about 20 wt. %, and in a still further aspect from about 10 wt. % to about 15 wt. %, based on the total weight of the composition. The foregoing weight percentages are calculated on an anhydrous metal salt basis.

In the laboratory examples, a PEC was formed by mixing aqueous solutions of Gantrez® S-95, or Gantrez® S-97 with a copolymer containing vinyl pyrrolidone (VP) and methacrylamidopropyl trimethylammonium chloride (MAPTAC) as described above. However, in general combinations of anionic and cationic polymers that form discrete particulates will also have applicability in this application.

Figure 2:
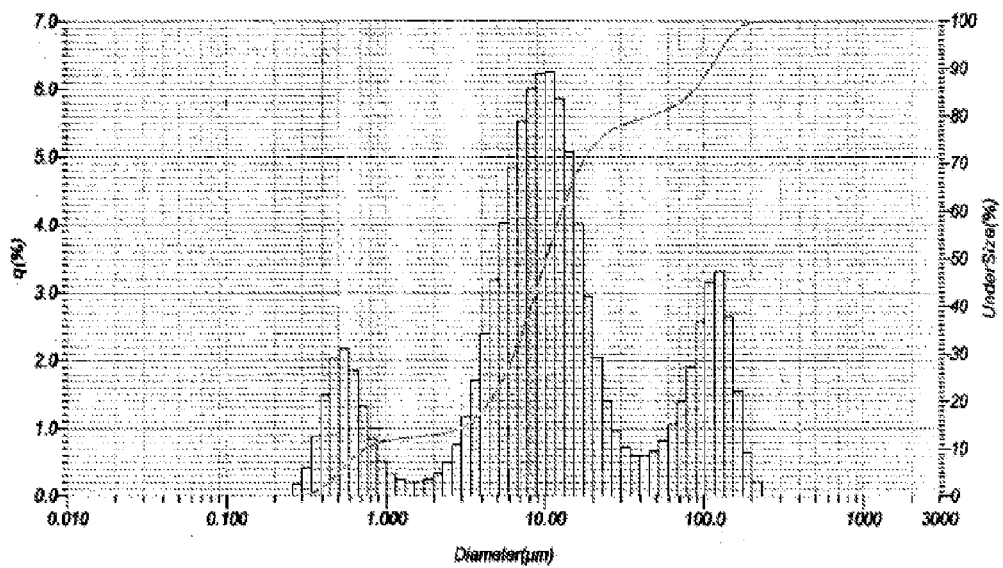
FIG. 2 is a graphical plot of particle size distribution for a 2.2% Gantrez® S-97:Conditioneze® NT-20 PEC:6.7% activated aluminum chlorohydrate aqueous mixture.
Figure 3:
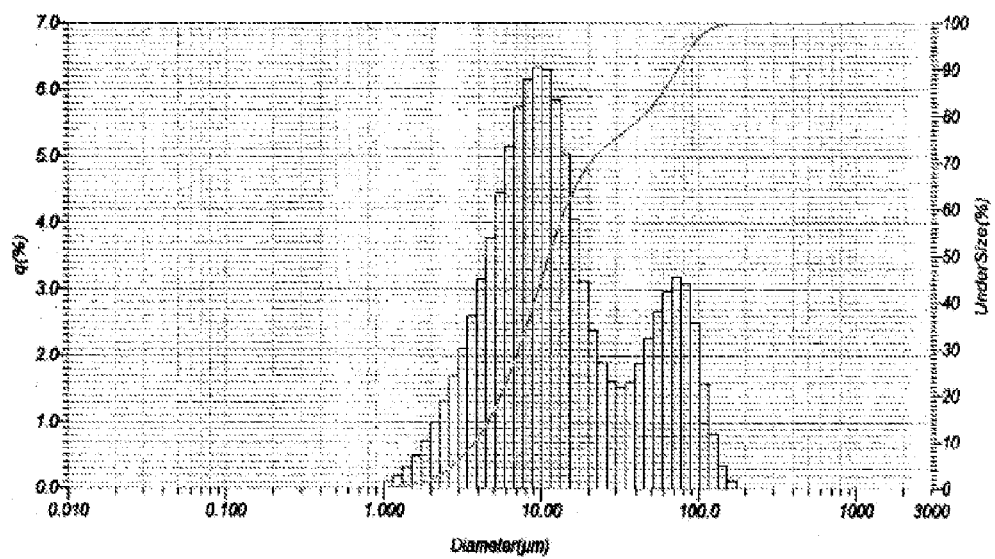
FIG. 3 is a graphical plot of particle size distribution for a 2.2% Gantrez® S-97:Conditioneze® NT-20 PEC:2.2% activated aluminum chlorohydrate; 4.4% $CaCl_2$.

The discrete bioadhesive particles typically are small enough to enter the pores of the sweat gland thereby forming polymeric plugs to impart sweat reduction. Further, by mixing the polymer complex with divalent salts, such as calcium, magnesium, and zinc, or aluminum salts, such as those used in antiperspirant formulations, it is possible to alter the particle size of the microgel. For example, FIG. 1 represents the particle size distribution of an aqueous 4% Gantrez® S-97: Conditioneze® NT-20 PEC alone. FIG. 2 is a 2.2% Gantrez® S-97:Conditioneze® NT-20 PEC:6.7% activated aluminum chlorohydrate (AACH) aqueous mixture. FIG. 3 is a formulation containing 2.2% Gantrez® S-97:Conditioneze® NT-20 PEC:2.2% AACH:4.4% $CaCl_2$. Note that in FIGS. 2 and 3 individual particles exist after addition of the aluminum salt and no bulk gelling is observed. Furthermore, the microgel structure becomes multi-modal, even though it is still composed of particles.

Figure 4:
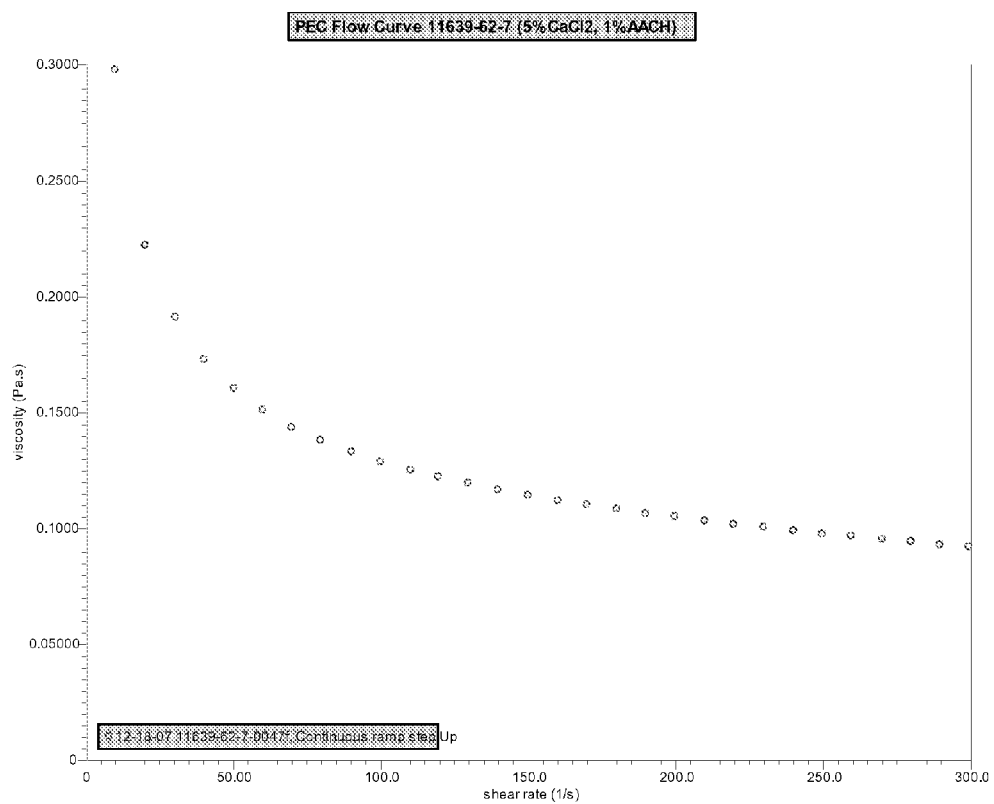
FIG. 4 is a Flow Curve for Gantrez® S-97:Conditioneze® NT-20 PEC with 5% $CaCl_2$ and 1% activated aluminum chlorohydrate.

As suggested in the rheogram depicted in FIG. 4, the resulting mixtures typically are cream-like dispersions that are shear-thinning and easily spreadable. Further, when applied to the skin and dried, the films may be clear, colorless, and continuous. The latter characteristic implies that sweat reduction efficacy may be based on a mixed pore-blocking and barrier film mechanism.

Compositions in accordance with certain aspects of the present invention may be formulated with various other excipients to improve performance. For example, plasticizers, such as Oleth or Brij (i.e., polyoxyethylene alkyl ethers) may be useful to plasticize antiperspirant film.

Procedure to Prepare PEC Complex

PEC complex was prepared in the following procedures as exampled with Polyquatemium 28 (Conditioneze NT-20) and Polymethylvinyl ether/maleic acid (Gantrez S-97).

1) Preparation of Stock Solutions of the Polymers

| Batch A: 4% active Gantrez S-97 Solution | % W/W | SUPPLIER |
|---|---|---|
| Water | 84.73 | |
| Sodium Hydroxide (10.00% active) | 11.27 | |
| PVM/MA Copolymer (Gantrez ® S-97) (100% active) | 4.0 | ISP |
| | 100.00% | |

Note:
In order to neutralize the Gantrez S-97, a 1:2.7 ratio of polymer to 10% NaOH solution was used to produce a pH of 7.

Procedure:
1. Add water to main tank. Mix with propeller blade.
2. Sprinkle Gantrez S-97 into vortex.
3. Add Sodium Hydroxide and mix until uniform.

| Batch B: 4% active Conditioneze NT-20 Solution | % W/W | SUPPLIER |
|---|---|---|
| Water | 80.49 | |
| Polyquaternium-28 (Conditioneze ® NT-20) (20.5% active) | 19.51 (4% active) | ISP |
| | 100.00% | |

Batch C: 4% Complex Solution, Concentrate

Procedure:
Add 45 parts of Batch B, 4.00% active aqueous solution of Conditioneze® NT-20, to main container and mix with moderate to fast (1000-1200 rpm) propeller agitation. Add 5 parts of Batch A, 4.00% active Gantrez® BF Polymer S-97 solution, to Conditioneze® NT-20 solution over the course of about 20-30 seconds. Mix for ten minutes.

| Appearance of PEC complex: | thin, milky-white liquid pH: |
|---|---|
| pH: | 7.13 |

The 4% complex concentrate can be diluted to appropriate usage levels.

Table 1 shows some examples of the polyelectrolyte compositions useful in accordance with certain aspects of this invention.

TABLE 1

| | | PEC Examples | | | | |
|---|---|---|---|---|---|---|
| Ingredients INCI name | Trade name | EXP. 1 WT. % | EXP. 2 WT. % | EXP. 3 WT. % | EXP. 4 WT. % | EXP. 5 WT. % |
| Polymethylvinyl ether/maleic acid | Gantrez ® S-97 | 0.20 | 0.10 | 0.30 | 0.40 | 0.15 |
| NaOH, 10% Neutralizing agent | | 0.56 | 0.27 | 0.38 | 1.12 | 0.19 |
| Polyquaternium-28 | Conditioneze ® NT-20 | 1.80 | 1.0 | 2.8 | 4.0 | 1.5 |
| Water | | BAL | BAL | BAL | BAL | BAL |

Other PEC's include those made by neutralizing Gantrez, or other polyacids, with other neutralizers to obtain more complex PEC's (Table 2).

TABLE 2

| Various PEC Combinations | | |
|---|---|---|
| Anionic Polymer | Cationic Polymer | Neutralizer |
| Gantrez S-95 | NT-20 | NaOH |
| Gantrez S-97 | NT-20 | NaOH |
| Gantrez S-97 | NT-20 | $CaCO_3$/KOH |
| Gantrez S-97 | NT-20 | $SrCO_3$/KOH |
| Gantrez S-97 | 0.75 NT-20/0.25 W-20 | $CaCO_3$/KOH |

TABLE 2-continued

Various PEC Combinations

| Anionic Polymer | Cationic Polymer | Neutralizer |
|---|---|---|
| Gantrez S-97 | 0.75 NT-20/0.25 W-20 | $SrCO_3$/KOH |
| 1:1 S-95:S-97 | NT-20 | $CaCO_3$/KOH |
| 1:1 S-95:S-97 | NT-20 | $SrCO_3$/KOH |
| Gantrez S-97 | NT-20 | $ZnCO_3$/KOH |
| Gantrez S-97 | NT-20 | $CuCO_3$/KOH |
| pIB/Man (5013) | NT-20 | KOH |
| 1:1 HMW Gantrez-S/5013 | NT-20 | KOH |
| Poly(Sodium polystyrene sulfonate) | NT-20 | — |
| ACP-1001 | NT-20 | KOH |
| Acrylidone LM | NT-20 | KOH |
| P(IB/MAn/MVE) | NT-20 | KOH |
| Sodium alginate | NT-20 | — |
| Sodium carboxymethyl cellulose | NT-20 | — |
| UltraThix P-100 | NT-20 | KOH |

The PECs in Table 2 were all prepared similarly. The original PEC's were made by preparing 4% solutions of Conditioneze NT-20 and Gantrez S-9x. After formation, the two solutions were mixed together (anionic solution slowly poured into the higher volume cationic solution) at high agitation with a 2-inch diameter Jiffy mixer.

Ethanol-Containing PEC's:

PEC's used in this application may be prepared in up to 60% alcohol (Table 3)—although ethanol was used for the following compositions, other solvents or solvent mixtures that solubilize the polymers and disperse the microgels may also be used.

TABLE 3

Description of Alcohol-Containing PEC's

| Exp. | Description | % Solids/% Alcohol level |
|---|---|---|
| 6 | NT-20:S-97 (Ca++/K+) | 4/27 |
| 7 | NT-20:5013 | 4.4/33.3 |
| 8 | NT-20:5013/HMW S (Ca++/K+) | 4.4/33.3 |
| 9 | NT-20:UltraThix P100 | 4.6/33.1 |
| 10 | NT-20:S-97 (Ca++/K+) | 6.7/30 |
| 11 | NT-20:UltraThix P100 | 6.9/29.8 |
| 12 | NT-20:5013 | 6.7/30 |

Table 7 summarizes the results for some additional PEC's that were tested with and without aluminum chlorohydrate (ACH). In all systems the 1% ACH systems behaved better than systems with PEC alone. Alcohol improves drying time and allows a route to increasing the product solids through ethanol removal.

Although not wishing to be bound by theory, it is believed that at low active ingredient levels, the primary reason for sweat reduction using PEC technology is pore blocking. Because this mechanism is much simpler than the mixed and complex sweat-reduction mechanism introduced by aluminum-based antiperspirant salts, an in-vitro screening method to test for pore-blocking based antiperspirancy was developed. The method, which is based on the presence or lack of formation of the blue starch-iodine complex, includes an apparatus constructed so that water vapor can only escape through the mesh sandwich. If the pores of the coated nylon mesh plug with formula, then the water vapor cannot pass and the starch spot covering the hole will remain white (although some dark brown iodine discoloration may appear in the starch over extended time periods). If the test formula fails to plug the mesh pores, water vapor will carry the iodine sitting above it up to the starch and stain it purple. The color of the purple stain will vary with the relative degree of pore clogging failure. The density of the spot can be measured using a densitometer or colorimeter. In accordance with the following test procedure, the total color difference ($\Delta E^*$) is calculated for the test samples as an indication of the efficacy of the formulation.

The in-vitro procedure below has been developed based on the starch/iodine purple staining test utilized on human subjects. The necessary equipment is as follows:
30 ml capacity, wide mouth glass jar
4.5 cm diameter, foamed polyethylene lined lid to fit the 30 ml jar
7.3 cm diameter, 64 micron pore size nylon mesh (McMaster-Carr item no. 9318T22)
3.8 cm diameter, 64 micron pore size nylon mesh
5 cm wide packaging tape (Henkel 2003/13862 or similar)
Water soluble starch (Fluka 33615)
15% iodine in ethanol solution
Distilled or deionized water
Forced air oven set at 32° C.

The test procedure is described below:

1. A 7.3 cm diameter nylon mesh circle is coated with an AP/DEO formula and dried to constant weight at 32° C. in the forced air oven. A dried coating weight of 0.2-0.3 grams is targeted. Duplicates or triplicates for each subject formula are prepared.

2. A 2.54 cm hole is drilled or punched in both the jar lid and its liner with an appropriate tool. Care must be taken so that the plastic jar lid is not cracked during this process.

3. 10 grams of water are added to the glass jar.

4. An approximate 2.7 cm circle of starch is coated onto the center of a (roughly) 10 cm length of packaging tape. This circular spot can be accomplished by simply pouring a small amount of starch through a hollow tube that has been securely positioned on the adhesive strip. Excess starch is tapped off the tape strip by inverting the tape/tube combination before tube removal.

5. The 3.8 cm diameter nylon mesh is stained with the iodine solution in a hood. Once the ethanol has evaporated, the stained nylon circle is placed in the jar lid.

6. The coated larger piece of nylon mesh is gently centered over the water filled jar opening. Care is taken so that the coating integrity is not compromised.

7. The jar is carefully sealed with the lid containing the iodine spotted mesh. The coated mesh now faces the water reservoir below. The iodine stained mesh sits above the coating. Again, care must be taken so that the coating integrity is not disturbed.

8. The starch stained tape is placed squarely over the lid's hole. The tape borders are sealed to the lid by hand pressure.

Two PEC formulations were tested in accordance with the foregoing in vitro test method. The purple spotting patterns and intensity suggest that the Gantrez® S-95:Conditioneze® NT-20 PEC+1% AACH system performed slightly better than the Gantrez® S-97:Conditioneze® NT-20 PEC+1% AACH system. In accordance with the described test method, "white" depicts no moisture permeability (indicating a positive result) and "blue/purple" indicates a negative result. Parafilm results in a positive result while Sure® solid results in a "blue/purple" spot indicating significant moisture permeability.

To validate the newly developed in-vitro sweat reduction assay, the PEC+1% AACH sample was tested vs. a negative control. This in-vivo test mimicked the in-vitro test—however, instead of applying the AP material to a mesh, the material was applied in a rubbing motion to the dry forearm of the subject. After the product dried, the iodine and starch were applied as in the in-vitro method and the apparatus was fastened to the forearm via the ends of the adhesive tape. The subject was positioned in an environment of 90-100° F. for 15 minutes, after which the test swatches were immediately removed and placed on silicone release paper to air dry. The results of the assay are provided in Table 1. The images and ΔE*trends from colorimetry in Tables 2 and 3 clearly depict the sweat reduction efficacy of the PEC (S-95)+1% AACH system.

TABLE 4

Summary of In-Vivo Colorimetry Test Strip Results

| Formula | Temp/Time | Position on arm | ΔE* |
|---|---|---|---|
| None | 94° F./15 min | Elbow | 40.14 |
|  |  | Middle | 33.90 |
|  |  | Wrist | 36.18 |
| PEC-11 | 94° F./15 min | Elbow | 10.88 |
| 1% AACH + 3.8% S-95:NT-20 PEC |  | Middle | 9.51 |
|  |  | Wrist | 23.97 |
| Comparative Examples |  |  |  |
| DK300 AN (anhydrous slurry) | 104° F./15 min | Elbow | 27.02 |
| 1% AACH + 15% CaCl$_2$ + 4% S-97 |  | Middle | 14.11 |
|  |  | Wrist | 32.40 |
| DK300 #2 | 104° F./15 min | Elbow | 16.00 |
| 1% AACH + 15% CaCl$_2$ + 4% S-97 |  | Middle | 26.15 |
|  |  | Wrist | 27.69 |

TABLE 5

Summary of In-Vitro Colorimetry Test Strip Results

| Formula | Mesh Size (um) | Temp/Time | ΔE* |
|---|---|---|---|
| Sure Solid | 64 | 32 C./1 hr | 36.20 |
| Sure Solid | 64 | 32 C./1 hr | 30.18 |
| PEC-10 S-97:NT-20 w/1% AACH | 64 | 32 C./2 hrs | 11.24 |
| PEC-10 S-97:NT-20 w/1% AACH | 64 | 32 C./2 hrs | 8.76 |
| PEC-11 S-95:NT-20 w/1% AACH | 64 | 32 C./2 hrs | 4.86 |
| PEC-11 S-95:NT-20 w/1% AACH | 64 | 32 C./2 hrs | 4.25 |

The following formulations were prepared without aluminum to see the interaction of a standard Gantrez S-9x:Conditioneze NT-20 PEC with various inorganic, non-aluminum-containing, multivalent salts (Table 6).

TABLE 6

Interaction of Gantrez S-95:NT-20 PEC with Various Salts

| 4% PEC-S95 (g) | Salt | Amt. Salt (g) | Water (g) | ΔE* In-vitro |
|---|---|---|---|---|
| 9.4 | KAuCl$_4$ | 0.1 | 0.5 | 31 |
| 9.4 | SrCO$_3$ | 0.1 | 0.5 | 23 |
| 9.4 | ZrOCl$_2$•8 H$_2$O | 0.1 | 0.5 | 22 |
| 9.4 | ZrCO$_3$ | 0.1 | 0.5 | 16 |
| 9.4 | SrHPO$_4$ | 0.1 | 0.5 | 13 |
| 9.4 | Zr(HPO$_4$)$_2$ | 0.1 | 0.5 | 30 |
| 9.4 | TiO$_2$ | 0.1 | 0.5 | 8 |
| 9.4 | ZnO | 0.1 | 0.5 | 8 |

The in-vitro results show that TiO$_2$ and ZnO nanoparticles with the S-95 PEC may have significant SWR (sweat weight reduction) efficacy.

TABLE 7

In-vivo Results (elbow) for PEC's with & without ACH

| PEC Description/Formulation | In-vivo result* |
|---|---|
| UltraThix P-100:NT-20 only | Spotty |
| UltraThix P-100:NT-20 + 1% ACH | Excellent |
| Acrylidone LM:NT-20 only | Some efficacy |
| Acrylidone LM:NT-20 + 1% ACH | Excellent |
| Gantrez S-97:NT-20, 30% ethanol only | Poor |
| Gantrez S-97:NT-20, 30% ethanol + 1% ACH | Excellent |
| Gantrez S-97 (Ca$^{++}$/K$^+$ salt):NT-20, 30% ethanol only | Very good |
| Gantrez S-97 (Ca$^{++}$/K$^+$ salt):NT-20, 30% ethanol + 1% ACH | Excellent |
| Gantrez S-97 (Ca$^{++}$/K$^+$ salt):NT-20-W-20 (75:25 w/w) only | Excellent |
| Gantrez S-97 (Ca$^{++}$/K$^+$ salt):NT-20-W-20 (75:25 w/w) + 1% ACH | Excellent |

Key: *= mid-forearm, 95-105° F.

The ratio of Gantrez S to Conditioneze NT-20 for the PEC's used in the table is 10% Gantrez S-9x:90% Conditioneze NT-20.

The PEC-based AP actives are water-based materials and may be easily added into water-based antiperspirant formulations. Further, dispersions in non-aqueous aerosol systems can also be prepared.

What is claimed is:

1. An antiperspirant microgel comprising:
    a) an active antiperspirant ingredient selected from the group consisting of titanium dioxide or zinc oxide and
    b) a polyelectrolyte complex comprising
        (i) polyquaternium-28
        (ii) polyvinylmethyl/maleic acid copolymer
        wherein the charge ratio of (i):(ii) is from about 0.70 to about 1.80; and wherein the microgel has an average particle size sufficient to allow the antiperspirant microgel to enter a human sweat gland pore and form a polymeric plug therein, wherein the antiperspirant microgel has an antiperspirant effect.

2. The microgel according to claim 1 wherein the charge ratio is about 0.90 to about 1.50.

3. The microgel according to claim 1 wherein the charge ratio is 1.

4. The microgel according to claim 1 wherein the average microgel particle size is about 0.2 μm to about 100 μm.

5. The microgel according to claim 4 wherein the average particle size is about 5 μm to about 60 μm.

6. The microgel according to claim 1 wherein the mole ratio of the polyvinylmethyl/maleic acid copolymer to the polyquaternium-28 polymer at pH 7 is from about 1.39 to about 3.06.

7. The microgel according to claim 6 wherein the mole ratio is from about 1.50 to about 2.55.

8. The microgel according to claim 1 wherein the weight ratio of the polyquaternium-28 polymer to the polyvinylmethyl/maleic acid copolymer is from about 6 to 15.

9. The microgel according to claim 8 wherein the weight ratio is from 7.0 to 11.91.

10. The microgel according to claim 1 wherein the weight ratio of the polyquaternium-28 polymer to the polyvinyl methyl/maleic acid copolymer is from about 2.44 to about 5.37.

11. The microgel according to claim 10 wherein the weight ratio is from 2.68 to 4.47.

12. The micro gel according to claim 1 further comprising an aluminum salt.

13. The microgel according to claim 1 wherein the active antiperspirant ingredient is from 0.5 weight percent to 35 weight percent of the microgel.

14. A method of reducing sweat production from a human sweat gland comprising applying the antiperspirant microgel according to claim 1 to pores of a human sweat gland.

15. A method of preparing the antiperspirant microgel according to claim 1 comprising combining the polyvinylmethyl/maleic acid copolymer and polyquaternium-28 in an amount of solvent effective to solubilize the anionic copolymer and cationic copolymer and disperse the microgels.

16. The method according to claim 15 wherein the solvent is water.

17. The method according to claim 15 wherein the solvent is 60% ethanol in water.

18. An antiperspirant microgel comprising a polyelectrolyte complex of
   (i) polyquaternium-28
   (ii) polyvinylmethyl/maleic acid copolymer
   wherein in the charge ratio of (i):(ii) is from about 0.70 to about 1.80;
   (iii) a multivalent metal salt selected from the group consisting of titanium dioxide or zinc oxide; wherein
   the microgel has an average particle size sufficient to allow the microgel to enter a human sweat gland pore and form a polymeric plug therein, wherein the antiperspirant microgel provides an antiperspirant effect;
and wherein the microgel is substantially free of an aluminum salt.

19. A method of reducing sweat in a human in need thereof comprising applying to pores of the human's sweat glands a microgel comprising a polyelectrolyte complex comprising
   (i) a cationic polyquaternium polymer; and
   (ii) an anionic copolymer comprising mono-, di- or tri-acid groups, or salts thereof;
   wherein in the charge ratio of (i):(ii) is from about 0.70 to about 1.80; and
an average microgel particle size sufficient to allow the microgel to enter a human sweat gland pore and to form a polymeric plug therein.

20. An antiperspirant microgel consisting essentially of
   a) a polyelectrolyte complex of
      (i) polyquaternium-28; and
      (ii) polyvinylmethyl/maleic acid copolymer and
   b) a titanium dioxide or zinc oxide nanoparticle;
   wherein in the charge ratio of (i):(ii) is from about 0.70 to about 1.80; and wherein the microgel has an average particle size sufficient to allow the microgel to enter a human sweat gland pore and form a polymeric plug therein providing an antiperspirant effect.

21. The microgel according to claim 20 having 1% by weight titanium dioxide nanoparticles.

22. The microgel according to claim 20 having 1% by weight zinc oxide nanoparticles.

* * * * *